United States Patent
Pedrosa Martins et al.

(10) Patent No.: US 12,233,145 B2
(45) Date of Patent: Feb. 25, 2025

(54) ULTRA-VIOLET ABSORBING COMPOUNDS

(71) Applicants: CIIMAR—CENTRO DE INVESTIGACAO MARINHA E AMBIENTAL, Oporto (PT); UNIVERSIDADE DO PORTO, Oporto (PT); FACULTY OF SCIENCES, CHOUAIB DOUKKALI UNIVERSITY, El Jadida (MA)

(72) Inventors: Teresa Patricia Pedrosa Martins, Matosinhos (PT); Mariana Alves Reis, Matosinhos (PT); Pedro Nuno Da Costa Leao, Matosinhos (PT); Vitor Manuel Oliveira Vasconcelos, Matosinhos (PT); Meryem Hassouani, El Jadida (MA); Brahim Sabour, El Jadida (MA)

(73) Assignees: CIIMAR—CENTRO INTERDISCIPLINAR DE INVESTIGACAO MARINHA E AMBIENTAL, Matosinhos (PT); UNIVERSIDADE DO PORTO, Oporto (PT); FACULTY OF SCIENCES, CHOUAIB DOUKKALI UNIVERSITY, El Jadida (MA)

( * ) Notice: Subject to any disclaimer, the term of this patent is extended or adjusted under 35 U.S.C. 154(b) by 750 days.

(21) Appl. No.: 17/297,351

(22) PCT Filed: Jan. 2, 2020

(86) PCT No.: PCT/EP2020/050025
§ 371 (c)(1),
(2) Date: May 26, 2021

(87) PCT Pub. No.: WO2020/128112
PCT Pub. Date: Jun. 25, 2020

(65) Prior Publication Data
US 2022/0331218 A1    Oct. 20, 2022

(30) Foreign Application Priority Data

Dec. 21, 2018 (PT) .......... 115227

(51) Int. Cl.
*A61K 8/49* (2006.01)
*A61Q 17/00* (2006.01)
*A61Q 17/04* (2006.01)
*G02B 1/04* (2006.01)
*G02B 5/00* (2006.01)
*G02C 7/10* (2006.01)

(52) U.S. Cl.
CPC ............ *A61K 8/492* (2013.01); *A61Q 17/005* (2013.01); *A61Q 17/04* (2013.01); *G02B 1/041* (2013.01); *G02B 5/003* (2013.01); *G02C 7/10* (2013.01)

(58) Field of Classification Search
None
See application file for complete search history.

(56) References Cited

U.S. PATENT DOCUMENTS 5,498,405 A    3/1996    Gerwick et al.
6,787,147 B1 *    9/2004    Huner .................... C12P 23/00
424/59

OTHER PUBLICATIONS

Swain et al. ("Antibacterial, antifungal and antimycobacterial compounds from cyanobacteria", Biomedicine & Pharmacotherapy, vol. 90, 2017, pp. 760-776) (Year: 2017).*
C.S. Grant, et al; Scytonemin-imine, a mahogany-colored UV/Vis sunscreen of cyanobacteria exposed to intense solar radiation; Organic Geochemistry; vol. 65; Dec. 1, 2013; pp. 29-36; XP055683143.
International Search Report and Written Opinion for corresponding application PCT/EP2020/050025 dated Apr. 30, 2020.

* cited by examiner

*Primary Examiner* — Robert A Wax
*Assistant Examiner* — Quanglong N Truong
(74) *Attorney, Agent, or Firm* — LUCAS & MERCANTI, LLP

(57) ABSTRACT

Novel compounds able to absorb UV radiation and comprise antimicrobial properties as well. The compounds are novel and undisclosed scytonemin analogs, able to absorb up to 90% of UV-A radiation and can cover a broader UV to blue light absorption range from 293 nm to 500 nm. When mixtures of more than one compound are used, their synergetic absorption properties can cover an even broader spectrum within 293 nm to 500 nm. The compounds present faint coloration, and some are even colorless, therefor the present compounds can be easily incorporated in formulations to be used in cosmetic products, sunscreens or lenses for sunglasses.

13 Claims, 9 Drawing Sheets

ULTRA-VIOLET ABSORBING COMPOUNDS

CROSS-REFERENCE TO RELATED APPLICATIONS

This application is a 371 of PCT/EP2020/050025, filed Jan. 2, 2020, which claims the benefit of Portuguese Patent Application No. 115227, filed Dec. 21, 2018, each of which are incorporated herein by reference.

TECHNICAL FIELD

This application relates to novel ultra-violet absorbing compounds.

BACKGROUND ART

Ultraviolet (UV) radiation is the most harmful and mutagenic component of the solar spectrum, being the main cause of premature skin aging, eye damage and some forms of skin cancer [1]. In fact, UV is possibly responsible for 50-90% of the total reported skin cancers [2]. In 2018, there were nearly 300.000 new cases reported worldwide [3]. Despite UV-B (280-320 nm) effects, especially carcinogenic, have been well known for several years, UV-A (320-400 nm) harmful effects are commonly neglected. In fact, UV-A radiation represents 95% of all UV light that reaches the Earth's surface and can penetrate deeply into the skin and the eyes, affecting the connective tissue and blood vessels. This capacity leads to eye damaging, loss of skin elasticity, wrinkles and consequently, premature ageing [4]. Furthermore, recent studies indicate that UV-A can also stimulate skin cancer development [5,6]. In addition to UV radiation, recent studies also indicate that high energy visible (HEV), also known as blue-violet light (400-500 nm) may act as a silent and long-term aging energy, causing inflammation, wrinkles, hyperpigmentation and others [7]. With the daily used of electronic devices such as televisions, computers and mobile phones, the exposition to blue-light has increased significantly, creating a clear tendency in the market to develop broad range sunscreens and other sun care products that can protect from UV-A, UV-B and blue-light.

In Nature, microorganisms have developed several protection strategies against the UV radiation, including the production of specialized UV-protective compounds such as scytonemin. Scytonemin is a UV-protective compound largely and exclusively distributed among cyanobacteria species that can reduce up to 90% of the UV-A radiation that penetrates the cells [8, 9]. Structurally, scytonemin is a symmetrical dimeric indole-alkaloid pigment with an indole/phenolic skeleton designated as scytoneman [8]. This complex and highly conjugated aromatic structure allows the strong UV-A absorption, presenting a maximum absorption at 370 nm. To this date, the scytoneman skeleton has been found in four scytonemin analogs, namely dimethoxyscytonemin, tetramethoxyscytonemin, scytonin and scytonemin-imine [10, 11]. All these previously reported compounds have strong absorption in the visible region and therefore have intense colors.

Scytonemin was subject of patent for its anticancer (WO2001062900A1) [12, 13], antioxidative/anti-inflammatory activity (U.S. Pat. No. 5,498,405A) [14] and sunscreen application (U.S. Pat. Nos. 5,498,405A, 6,787,147B1). Despite the potential as UV protective agent, the use of scytonemins has been compromised by their dark colors, precluding cosmetic applications.

Derikvand, P, et al. (2016) have disclosed small dimeric molecules from cyanobacteria. The scytonemin analogs disclosed in the present application differ from those of the cited document in the sense that present very faint or no color at all, that the present analogs comprise several undisclosed substituents, and that these compounds are capable of absorbing radiation in a broader range from 200 nm to 550 nm, notably absorbing strongly in the UV-B region of the spectrum. The substitutions in the scytoneman skeleton leading to the shift in absorption profile that renders these molecules colorless or faint-colored were not anticipated and such properties have not been observed previously.

Thus, the novel scytoneman-like compounds reported in this application have the following advantages: novel structure, colorless or faint coloration and UV to blue light absorption range (293 nm to 500 nm). Furthermore, some of these molecules present interesting antimicrobial properties which were never reported for any molecule of this family. This property can be of great interest for the development of multifunctional ingredients for topical use. The scytoneman skeleton can be easily accessed and modified to match the structures herein disclosed through adaptation of currently known organic synthesis methodologies [15, 16] and because its biosynthetic pathway is known, fermentation in a heterologous host can also be used to produce these compounds in vivo [17].

SUMMARY

The present application relates to ultra-violet (UV) radiation absorbing compounds of reduced formula (A) and (C) and oxidized formula (B),

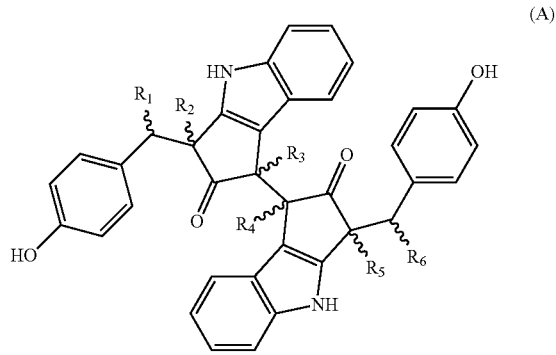

(A)

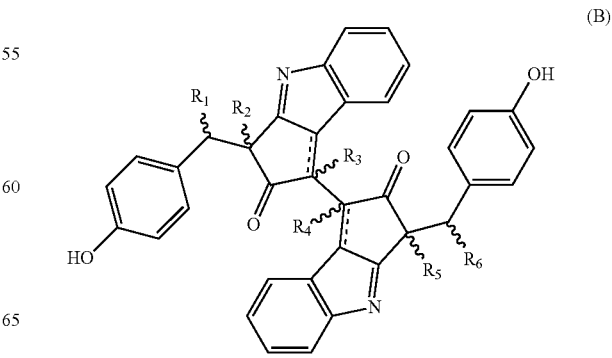

(B)

-continued

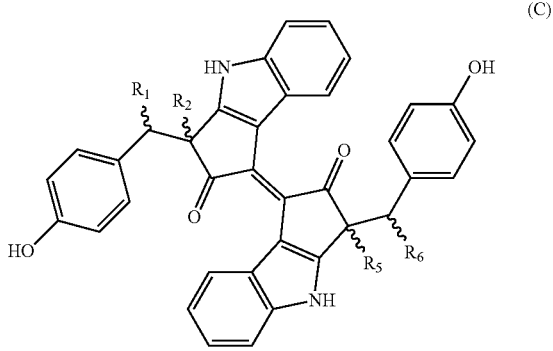

(C)

and stereoisomers thereof, wherein,

R1 and R6 are independently selected from H, OH, =O, $O(CH_2)_nCH_3$ where n=1-16, Br, Cl, N and S;

and R2, R3, R4 and R5 are independently selected from H, OH, $O(CH_2)_nCH_3$ where n=0-16, Br, Cl, N and S.

In one embodiment the compounds are 3'-hydroxyscytonemin, stereoisomers of 3'-hydroxy-3-methoxyscytonemin and stereoisomers of 3,3'-dihydroxyscytonemin.

In another embodiment the compounds absorb light from 293 nm to 500 nm.

In yet another embodiment the compounds absorb up to 90% of UV-A radiation.

In one embodiment the compounds have antimicrobial activity.

In another embodiment the compounds have antioxidant activity.

In one embodiment the compounds are for use in cosmetic products.

In another embodiment the compounds are for use in sunscreens.

In another embodiment the compounds are for use in sunglasses.

The present application also relates to formulations comprising the compounds.

In one embodiment the formulations comprise one compound.

In another embodiment the formulations comprise more than one compound.

In one embodiment the compounds are for use in cosmetic products.

In another embodiment the compounds are for use in sunscreens.

In yet another embodiment the compounds are for use in sunglasses.

General Description

The present application relates to novel compounds able to absorb UV radiation. In addition to providing protection against UV radiation, these compounds comprise antimicrobial properties as well.

The compounds herein described are novel and undisclosed scytonemin analogs from natural sources, particularly cyanobacteria, obtained from a Morocco environmental sample. Despite sharing the same basic structure, their absorption properties are quite different and so, used synergistically they can absorb light in a broad UV spectrum, offering a very efficient protection, precisely the function that they fulfil in the producing organisms. With these new compounds, the development of new active ingredients with enhanced UV-A protection that can be used in sun care products is proposed, namely in the formulation of sunscreens and/or embedded in the lenses of sunglasses and other surfaces in which this protection might be useful.

The presently described compounds present the following advantages:

The compounds can absorb up to 90% of UV-A radiation, fulfilling the need for UV-A protection;

The compounds are from natural sources—allowing to develop environmentally friendly products;

Formulations containing these compounds can cover a broader UV to blue light absorption range from 293 nm to 500 nm;

When mixtures of more than one compound are used, their synergetic absorption properties can cover an even broader spectrum within 293 nm to 500 nm;

These compounds can present faint coloration, and some are even colorless, overcoming the pigmentation problem occurring for other compounds that present strong colors, therefor the present compounds can be easily incorporated in a product;

These compounds also present antioxidant and antimicrobial properties, representing a major advantage for the development of multifunctional sunscreens.

The compounds herein described were isolated from cyanobacteria and bioactivity assays were performed in order to evaluate the properties of said compounds.

BRIEF DESCRIPTION OF DRAWINGS

For easier understanding of this application, figures are attached in the annex that represent the preferred forms of implementation which nevertheless are not intended to limit the technique disclosed herein.

DESCRIPTION OF THE EMBODIMENTS

Now, preferred embodiments of the present application will be described in detail with reference to the annexed drawings. However, they are not intended to limit the scope of this application.

Figure 1:
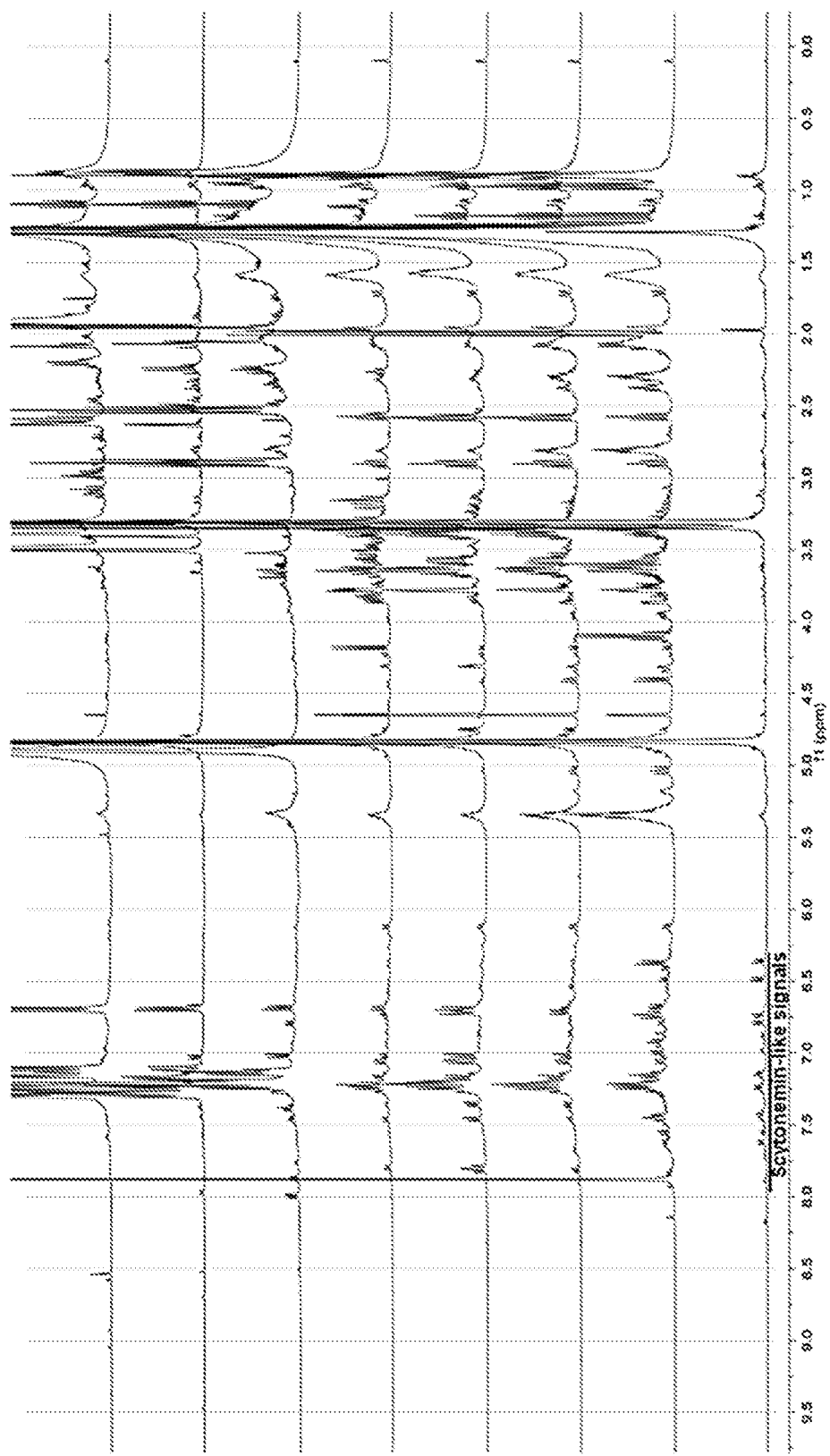
FIG. 1 shows the $^1H$ NMR spectra of several fractions presenting typical scytonemin-like signals.

The present application relates to scytonemin analogs (scytoneman-like compounds). The compounds were isolated from cyanobacteria collected from a small saltern pond located just behind the primary dune in Mrizika, Morocco (GPS coordinates: 32.955807, −8.779638). Morphological analysis allowed to classify the dominant cyanobacterium as a member of the Lyngbya genus. To explore the chemodiversity of the mat, the biomass was freeze-dried (650 g, d.w.) and extracted using a dichloromethane/methanol mixture (2:1). The crude extract was then fractionated by vacuum liquid chromatography using a solvent gradient with increasing polarity from 100% hexanes to 100% ethyl acetate and then to 100% MeOH. Fractions containing scytonemin-like signals in 1H NMR analysis were pooled and scytonemin was precipitated as described in the literature [8]. The filtered solution was subfractionated through flash chromatography using a gradient of hexanes, ethyl acetate to methanol. The resulting fractions were then analyzed by LC-HRMS, that revealed the presence of scytonemin and other major compounds whose calculated molecular formulas were consistent with scytoneman-like compounds, by only differing in a small number of atoms. The $^1$H NMR spectra of these fractions presented the typical aromatic signals between δ6.5 and 8 ppm, as well as OH signals between δ9 and 10 ppm as have been observed for the previously reported scytonemins—Table 1, FIG. 1.

TABLE 1

Identification of new scytoneman-like compounds by LC-HRMS analysis

Figure 2:
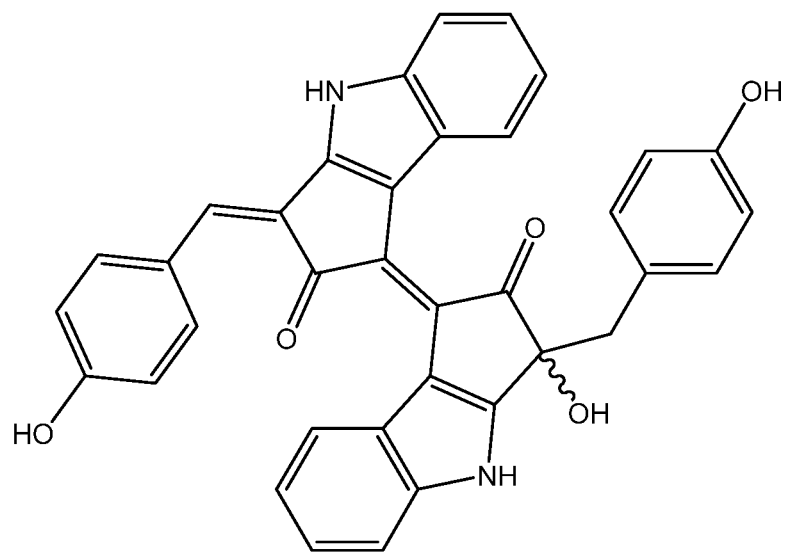
FIG. 2 shows the planar structure of 3'-hydroxyscytonemin ($C_{36}H_{24}O_5N_2$)—m/z [M-H]–: 563.1587.
Figure 3:
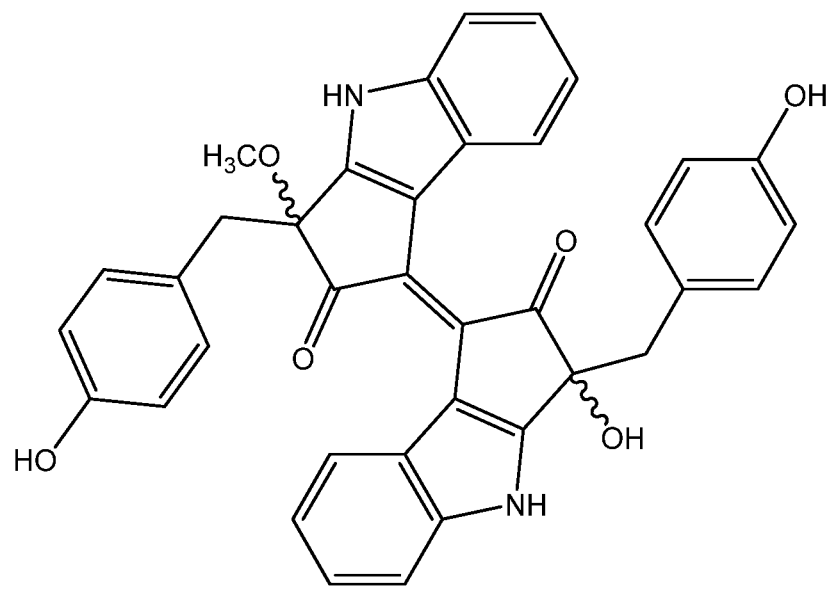
FIG. 3 shows the planar structure of 3'-hydroxy-3-methoxyscytonemins ($C_{37}H_{28}O_6N_2$)—m/z [M-H]–: 595.1864.
Figure 4:
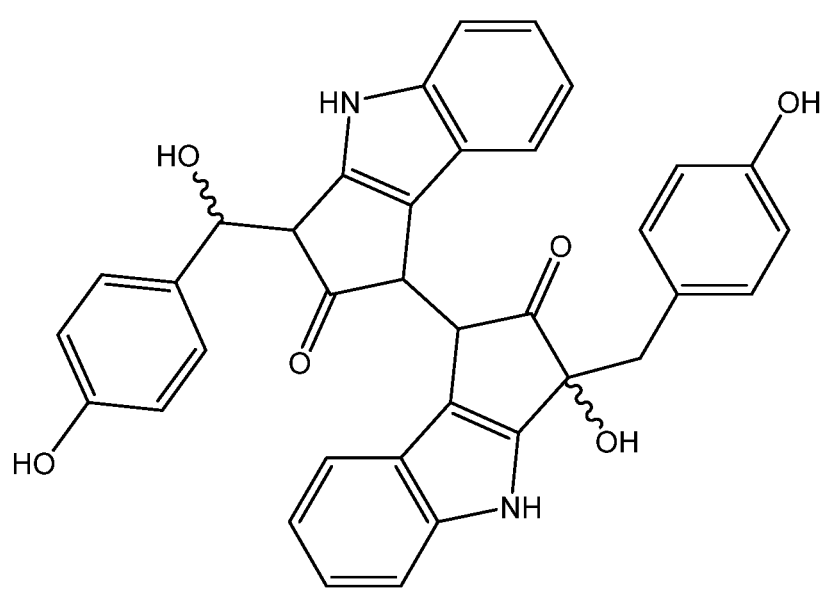
FIG. 4 shows the planar structure of 3,3'-dihydroxyscytonemin ($C_{36}H_{30}O_6N_2$)—m/z [M-H]–: 585.2061.

| m/z [M − H]⁻ | Chemical formula | Standard deviation/ppm | Difference to reduced scytonemin | Main absorbance regions |
| --- | --- | --- | --- | --- |
| 563.1587 a) | $C_{36}H_{24}O_5N_2$ | 3.55 | $+H_2O$ | UVA |
| 577.1369 | $C_{36}H_{22}O_6N_2$ | 5.30 | $+O_2$ | UVA |
| 579.1589 | $C_{36}H_{24}O_6N_2$ | 5.68 | $+HO_2$ | UVA/UVB |
| 581.1750 | $C_{36}H_{26}O_6N_2$ | 6.43 | $+H_3O_2$ | Green/Blue region |
| 585.2061 b) | $C_{36}H_{30}O_6N_2$ | 6.05 | $+H_8O_2$ | UVB |
| 591.1594 | $C_{37}H_{24}O_6N_2$ | 6.41 | $+CHO_2$ | UVA/blue region |
| 593.1742 | $C_{37}H_{26}O_6N_2$ | 4.95 | $+CH_3O_2$ | UVA |
| 595.1864 c) | $C_{37}H_{28}O_6N_2$ | 7.37 | $+CH_6O_2$ | Green/blue region |
| 609.1689 | $C_{37}H_{26}O_7N_2$ | 4.47 | $+CH_3O_3$ | UVA/blue region |
| 611.1853 | $C_{37}H_{28}O_7N_2$ | 5.68 | $+CH_5O_3$ | UVB |
| 657.1910 | $C_{38}H_{30}O_9N_2$ | 5.62 | $+C_2H_8O_5$ | UVB |
| 680.2218 | $C_{41}H_{33}O_8N_2$ | 8.72 | $+C_5H_{11}O_4$ | UVA |
| 673.1862 | $C_{38}H_{30}O_{10}N_2$ | 5.94 | $+C_2H_8O_6$ | UVB | a) Structure of the compound in FIG. 2
b) Structure of the compound in FIG. 4
c) Structure of the compound in FIG. 3

No bibliographic data has reported scytoneman-family compounds with the identified molecular masses, indicating that these compounds are new and had never been isolated or characterized. Based on this data, the new scytoneman compounds were isolated by reverse-phase HPLC using a gradient of water and acetonitrile, and performed their structural elucidation by NMR, 2D-NMR and HRMS2 techniques.

The new compounds present the general structure of reduced form of formula A and C, and oxidized formula B.

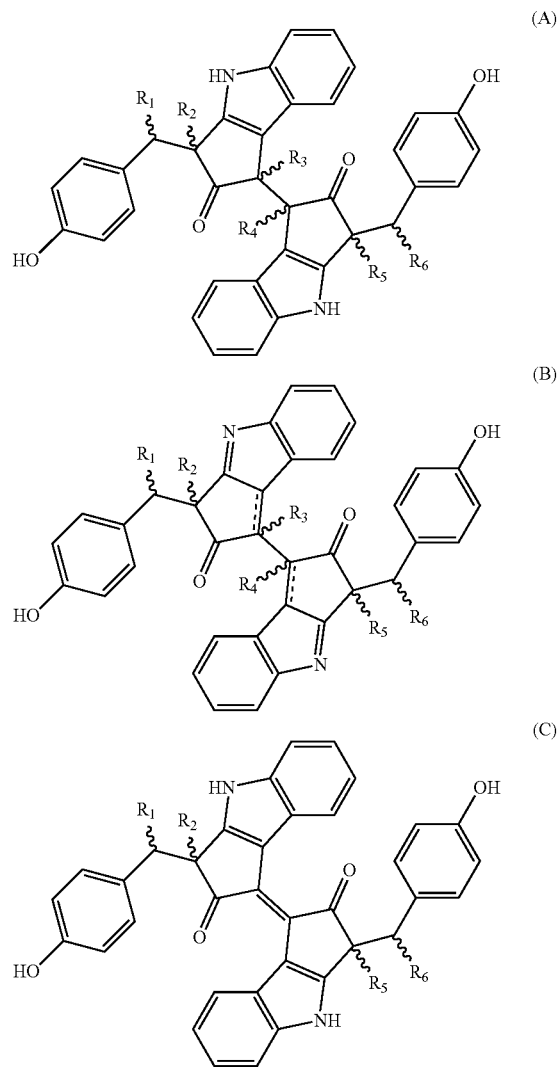

wherein,

And R1 and R6 are independently selected from H, OH, =O, $O(CH_2)_nCH_3$ where n=1-16, Br, Cl, N and S;

R2, R3, R4 and R5 are independently selected from H, OH, $O(CH_2)_nCH_3$ where n=0-16, Br, Cl, N and S.

In the reduced form C, R3 and R4 do not exist when the carbons, to which R3 and R4 are bond, are connected by a double bond.

Formula A relates to the reduced form of the molecule, with the indol group in NH form), and formula B relates to the oxidized form with the indol group in N form. The R and S isomers of the disclosed compounds are an object of protection of the present application as well.

More specifically, the following compounds were isolated: 3'-hydroxyscytonemin, two stereoisomers of 3'-hydroxy-3-methoxyscytonemin and two stereoisomers of 3,3'-dihydroxyscytonemin, as shown in FIGS. 2 to 4.

FIG. 2 shows the planar structure of 3'-hydroxyscytonemin (C36H24O5N2)—m/z [M-H]−: 563.1587.

FIG. 3 shows the planar structure of 3'-hydroxy-3-methoxyscytonemins (C37H28O6N2)—m/z [M-H]−: 595.1864.

FIG. 4 shows the planar structure of 3,3'-dihydroxyscytonemin (C36H30O6N2)—m/z [M-H]−: 585.2061.

Figure 5:
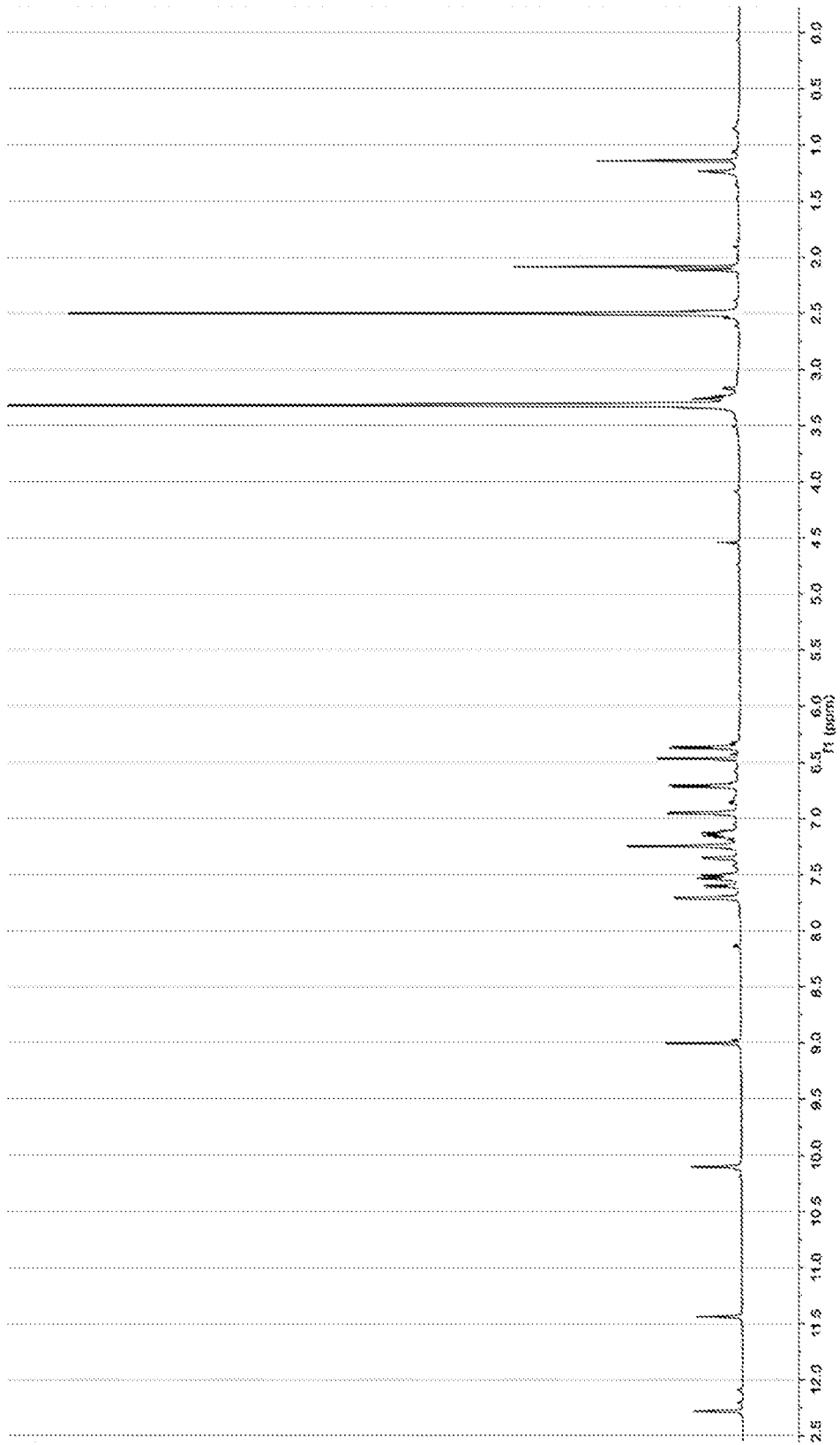
FIG. 5 shows the $^1H$ NMR spectrum (600 MHz, DMSO-d6) of compound 3'-hydroxyscytonemin.

Example of the Structural Elucidation for Compound: 3'-Hydroxyscytonemin:

The 1H NMR spectrum of 3'-hydroxyscytonemin, shown in FIG. 5, showed several characteristic singlet signals for scytonemins, that could be ascribed to two NH protons at 611.43 and 612.31 and two OH protons at 69.01 and 610.09. Furthermore, a proton resonating as singlet at 66.45, which is not found in the 1H NMR data of scytonemin, did not show a cross-peak in the HSQC data. This proton was assigned as belonging to an additional, when compared to scytonemin, hydroxyl group, satisfying the HRMS-derived molecular formula ($C_{36}H_{24}O_5N_2$).

Figure 6:
FIG. 6 shows the colors of scytonemin molecules at 1 mg/mL (from left to right): scytonemin (previously known), 3'-hydroxyscytonemin, 3'-hydroxy-3-methoxyscytonemin (isomer 1), 3'-hydroxy-3-methoxyscytonemin (isomer 2), scytonemin with the molecular formula $C_{36}H_{22}O_6N_2$ (isomer 1), scytonemin with the molecular formula $C_{36}H_{22}O_6N_2$ (isomer 2), 3,3'-dihydroxyscytonemin.

Although the new compounds present only slight differences in molecular composition when compared to scytonemin, these seem to strongly impact their UV-Vis absorption properties and their colors, as shown in FIG. 6. The previous role of scytonemin as a sunscreen active ingredient has been compromised by its dark color, seen in FIG. 6A, because products comprising the previously known dark scytonemin are not only not appealing to consumers, but also comprise the side effect of dying the fabrics that come in contact with such products. However, the different substitution pattern of these new scytonemins disrupts the conjugation of part of the molecules, leading to faint colored or even colorless compounds, overcoming this major issue that has been putting Cosmetic companies away from using these compounds.

Figure 7A:
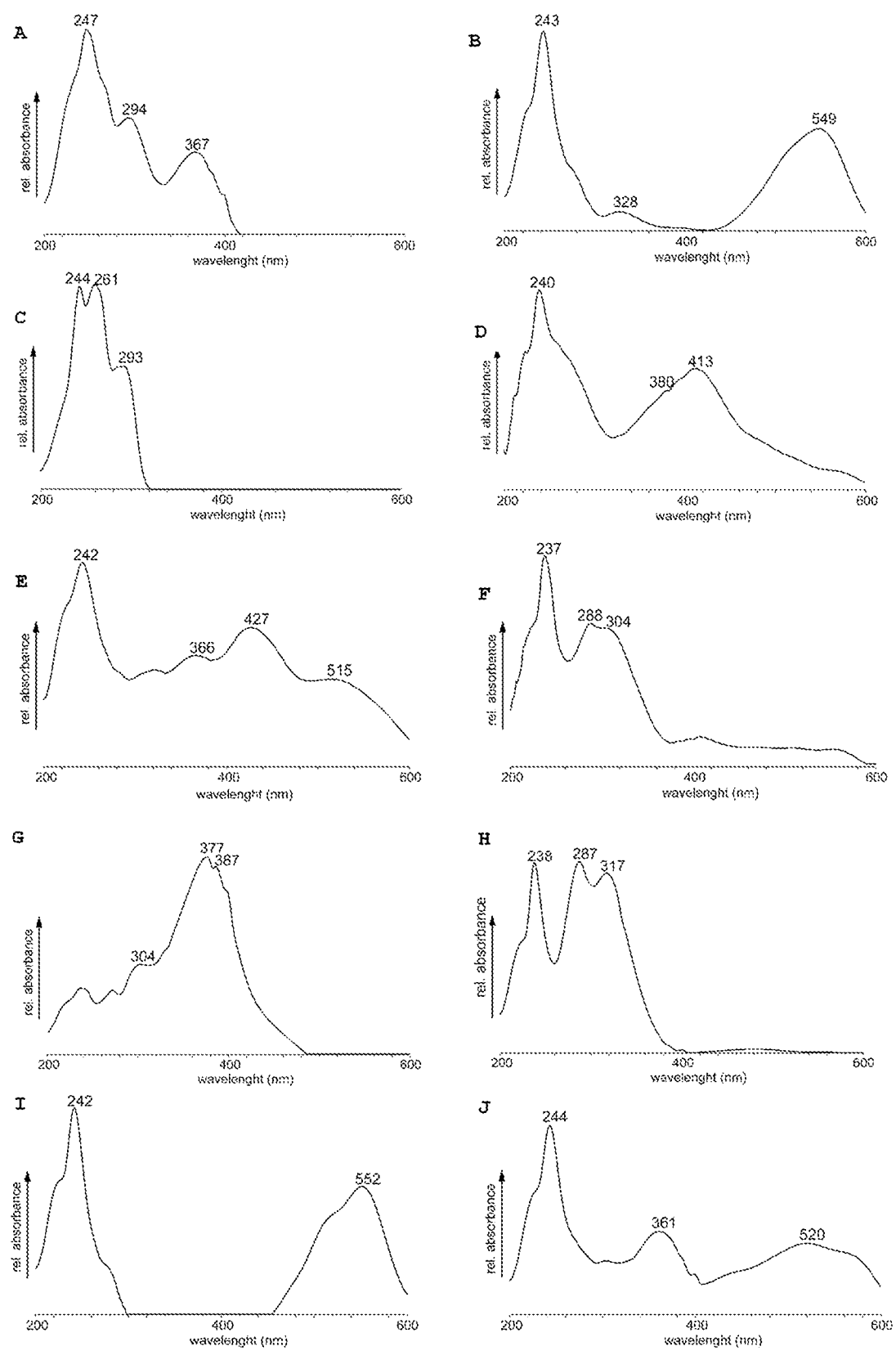
FIG. 7 shows the UV-Vis spectra of compounds m/z [M-H]–: 579.1589 (A), 581.1750 (B), 585.2061 (3,3'-dihydroxyscytonemin) (C), 591.1594 (D), 609.1689 (E), 611.1853 (F), 577.1369 (G), 673.1862 (H), 595.1864 (3'-hydroxy-3-methoxyscytonemins) (I), 593.1742 (J), 680.2218 (K), 657.1910 (L) and 563.1587 (3'-hydroxyscytonemin) (M)
Figure 7B:
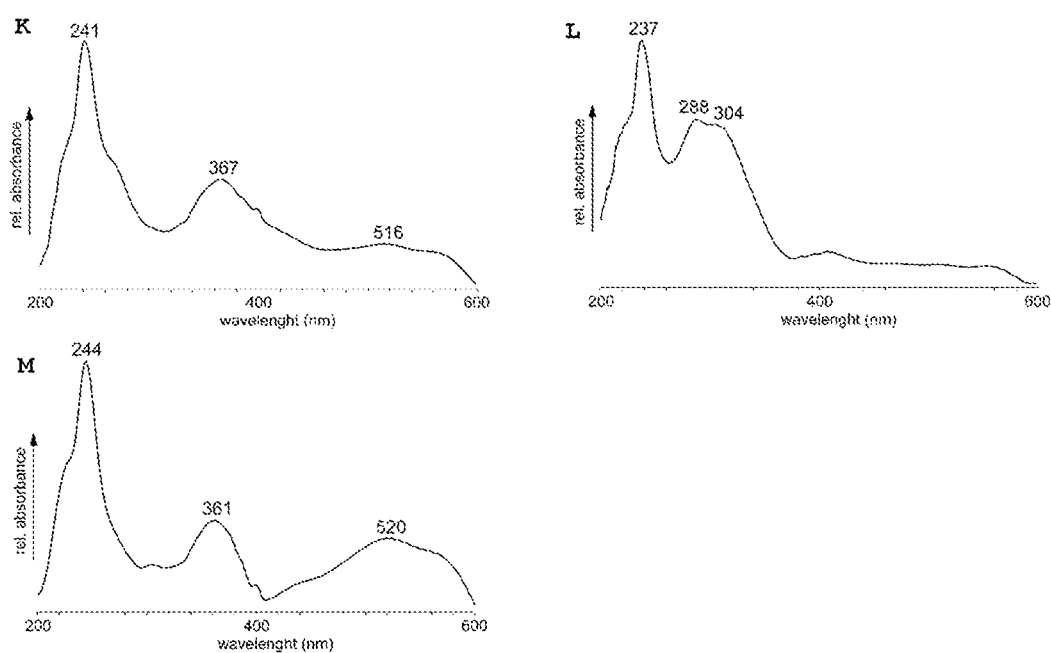

The UV absorption profiles for these molecules and the maximum absorption wavelength can be seen in FIG. 7 and table 2, respectively. This data provides an evidence of the complementarity action of the compounds, covering a very broad range of radiation from 293 nm to 500 nm. This indicates that when used as a mixture, they can provide an efficient protection against UV-B, UV-A and blue light.

TABLE 2

Maximum absorption wavelengths of the presently described compounds.

| m/z [M − H]− | Chemical formula | Main absorbance regions | Max wavelength (nm) |
|---|---|---|---|
| 563.1587 | $C_{36}H_{24}O_5N_2$ | UVA | 361, 520 |
| 577.1369 | $C_{36}H_{22}O_6N_2$ | UVA | 304, 377, 387 |
| 579.1589 | $C_{36}H_{24}O_6N_2$ | UVA/UVB | 294, 367 |
| 581.1750 | $C_{36}H_{26}O_6N_2$ | Green/Blue region | 549 |
| 585.2061 | $C_{36}H_{30}O_6N_2$ | UVB | 293 |
| 591.1594 | $C_{37}H_{24}O_6N_2$ | UVA/blue region | 290, 380, 413 |
| 593.1742 | $C_{37}H_{26}O_6N_2$ | UVA | 361 |
| 595.1864 | $C_{37}H_{28}O_6N_2$ | Green/blue region | 500, 552 |
| 609.1689 | $C_{37}H_{26}O_7N_2$ | UVA/blue region | 366, 427 |
| 611.1853 | $C_{37}H_{28}O_7N_2$ | UVB | 288, 304 |
| 657.1910 | $C_{38}H_{30}O_9N_2$ | UVB | 288, 304 |
| 680.2218 | $C_{41}H_{33}O_8N_2$ | UVA/UVB | 290, 367 |
| 673.1862 | $C_{38}H_{30}O_{10}N_2$ | UVB | 287, 317 |

Cytotoxicity Tests

Figure 8:
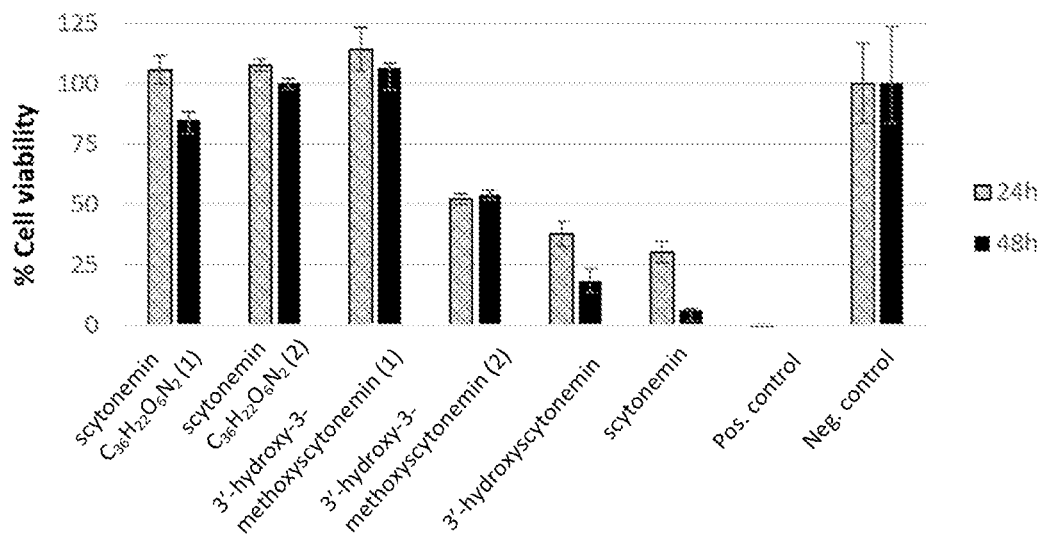
FIG. 8 shows the cytotoxicity assays results in SH-SY5Y cell line for the pure compounds scytonemin $C_{36}H_{22}O_6N_2$ (isomers 1 and 2), 3'-hydroxy-3-methoxyscytonemin (isomers 1 and 2), 3'-hydroxyscytonemin and the original scytonemin. 1% DMSO (v/v) was used as negative control and 20% DMSO (v/v) as a positive control.

The pure compounds were also tested in cytotoxicity assays using the MTT assay. Compound 3'-hydroxyscytonemin showed considerable bioactivity, reducing SY-SH5Y (neuroblastoma cell line) viability to 37.8% in 24 h and 18.3% in 48 h of exposure, at a final concentration of 10 μg mL$^{-1}$, as shown in FIG. 8.

Antimicrobial Activity

Figure 9:
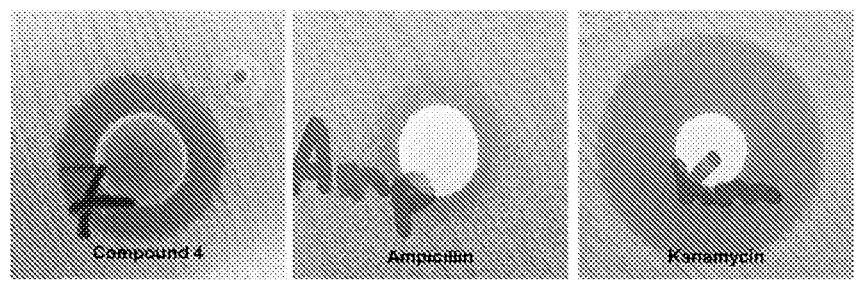
FIG. 9 shows the antibiograms of the novel compound 3'-hydroxyscytonemin (15 µg) against S. aureus ATCC 29213. Kanamycin and ampicillin (15 µg) were used as positive controls.

The pure compounds were also tested in antimicrobial assays using the disc diffusion method. Compound 3'-hydroxyscytonemin presented antimicrobial activity against *Staphylococcus aureus* (ATCC 29213) at a final concentration of 15 μg mL$^{-1}$, as shown in FIG. 9. Apart from its sunscreen function, the previously known scytonemins have been associated with anticancer and antioxidative activity, but no antimicrobial activity has ever been reported for any of the scytoneman family of compounds until now.

Synthesis

The scytoneman basic structure can be easily accessed and modified to match the structures herein disclosed through adaptation of currently known organic synthesis methodologies [2, 3] and because its biosynthetic pathway is known, fermentation in a heterologous host can also be used to produce this compound in vivo [4].

Application

Due to their extensive UV protection properties, the presently disclosed compounds can be used in formulations, particularly formulations for cosmetic products, sunscreens, lenses for sunglasses, or other applications, and thus complying with the need for UV-B, UV-A and blue light protection.

The fact that these compounds also present antimicrobial activity, combines yet another useful property with the UV protection.

In one embodiment the compounds are used in cosmetic products.

Additionally, in one embodiment these compounds can be used individually. In another embodiment the compounds are used in mixtures of more than one compound to extend the UV range of absorption.

In one embodiment, the formulations comprise one compound described herein. In another embodiment, the formulations comprise more than one compounds described herein.

This description is of course not in any way restricted to the forms of implementation presented herein and any person with an average knowledge of the area can provide many possibilities for modification thereof without departing from the general idea as defined by the claims. The preferred forms of implementation described above can obviously be combined with each other. The following claims further define the preferred forms of implementation.

REFERENCES

1. D'Orazio, J., et al., UV radiation and the skin. Int J Mol Sci, 2013. 14(6): p. 12222-48.
2. Kumar, R., G. Deep, and R. Agarwal, An Overview of Ultraviolet B Radiation-Induced Skin Cancer Chemoprevention by Silibinin. Curr Pharmacol Rep, 2015. 1(3): p. 206-215.
3. https://www.wcrf.org/dietandcancer/cancer-trends/skin-cancer-statistics
4. Krutmann, J., The role of UVA rays in skin aging. Eur J Dermatol, 2001. 11(2): p. 170-1.
5. Halliday, G. M., et al., UV-A fingerprint mutations in human skin cancer. Photochem Photobiol, 2005. 81(1): p. 3-8.

6. Gasparro, F. P., Sunscreens, skin photobiology, and skin cancer: the need for UVA protection and evaluation of efficacy. Environ Health Perspect, 2000. 108 Suppl 1: p. 71-8

7. Regazzetti, C., et al., Melanocytes sense blue-light and regulate the pigmentation through the Opsin 3. Journal of Investigative Dermatology, 2017. 137(10): p. S299-S299.

8. Garciapichel, F. and R. W. Castenholz, Characterization and Biological Implications of Scytonemin, a Cyanobacterial Sheath Pigment. Journal of Phycology, 1991. 27(3): p. 395-409.

9. Proteau, P. J., et al., The structure of scytonemin, an ultraviolet sunscreen pigment from the sheaths of cyanobacteria. Experientia, 1993. 49(9): p. 825-9.

10. Bultel-Ponce, V., et al., New pigments from the terrestrial cyanobacterium Scytonema sp. collected on the Mitaraka inselberg, French Guyana. J Nat Prod, 2004. 67(4): p. 678-81.

11. Grant, C. S. and J. W. Louda, Scytonemin-imine, a mahogany-colored UV/Vis sunscreen of cyanobacteria exposed to intense solar radiation. Organic Geochemistry, 2013. 65: p. 29-36.

12. Itoh, T., et al., Reduced scytonemin isolated from *Nostoc commune* suppresses LPS/IFNgamma-induced NO production in murine macrophage RAW264 cells by inducing hemeoxygenase-1 expression via the Nrf2/ARE pathway. Food Chem Toxicol, 2014. 69: p. 330-8.

13. Stevenson, C. S., et al., The identification and characterization of the marine natural product scytonemin as a novel antiproliferative pharmacophore. Journal of Pharmacology and Experimental Therapeutics, 2002. 303(2): p. 858-866.

14. Matsui, K., et al., The cyanobacterial UV-absorbing pigment scytonemin displays radical-scavenging activity. Journal of General and Applied Microbiology, 2012. 58(2): p. 137-144.

15. Ekebergh, A., et al., Oxidative coupling as a biomimetic approach to the synthesis of scytonemin. Org Lett, 2011. 13(16): p. 4458-61.

16. Ekebergh, A., A. Borje, and J. Martensson, Total synthesis of nostodione A, a cyanobacterial metabolite. Org Lett, 2012. 14(24): p. 6274-7.

17. Balskus, E. P., R. J. Case, and C. T. Walsh, The biosynthesis of cyanobacterial sunscreen scytonemin in intertidal microbial mat communities. Fems Microbiology Ecology, 2011. 77(2): p. 322-332.

The invention claimed is:

1. An ultra-violet (UV) radiation absorbing compound selected from 3'-hydroxyscytonemin and 3,3'-dihydroxyscytonemin of formulas:

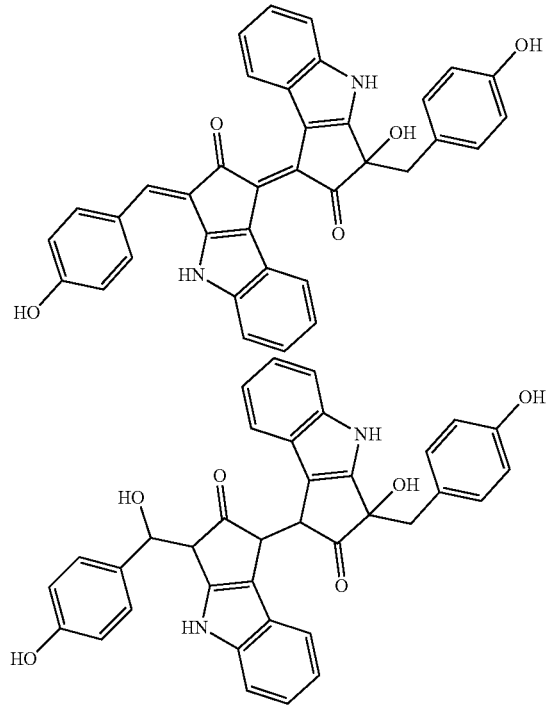

and stereoisomers thereof, wherein the compound has antibacterial activity.

2. The ultra-violet (UV) radiation absorbing compound according to claim 1, wherein the compound absorbs light from 293 nm to 500 nm.

3. The ultra-violet (UV) radiation absorbing compound according to claim 1, wherein the compound absorbs up to 90% of UV-A radiation.

4. The ultra-violet (UV) radiation absorbing compound according to claim 1, wherein the compound has antioxidant activity.

5. A cosmetic product comprising the ultra-violet (UV) radiation absorbing compounds of claim 1.

6. A sunscreen product comprising the ultra-violet (UV) radiation absorbing compounds of claim 1.

7. A pair of sunglasses comprising the ultra-violet (UV) radiation absorbing compounds of claim 1.

8. A formulation comprising the compounds of claim 1.

9. The formulation according to claim 8, wherein the formulation comprises one compound.

10. The formulation according to claim 8, wherein the formulation comprises more than one compound.

11. A cosmetic product comprising the formulation according to claim 8.

12. A sunscreen product comprising the formulation according to claim 8.

13. A lens for sunglasses comprising the formulation according to claim 10.

* * * * *